(12) United States Patent
Perisic

(10) Patent No.: US 9,421,114 B2
(45) Date of Patent: Aug. 23, 2016

(54) INTERSOMATIC CAGE

(71) Applicant: Michael Perisic, Zollikon (CH)

(72) Inventor: Michael Perisic, Zollikon (CH)

(73) Assignee: CARPE CONSULTANTS SARL (CH)

( * ) Notice: Subject to any disclaimer, the term of this patent is extended or adjusted under 35 U.S.C. 154(b) by 0 days.

(21) Appl. No.: 14/755,074

(22) Filed: Jun. 30, 2015

(65) Prior Publication Data

US 2015/0297358 A1   Oct. 22, 2015

Related U.S. Application Data

(62) Division of application No. 12/993,960, filed as application No. PCT/IB2009/005721 on May 26, 2009, now Pat. No. 9,289,314.

(30) Foreign Application Priority Data

| May 26, 2008 | (CH) | 0794/08 |
| May 26, 2008 | (CH) | 0795/08 |
| Jun. 6, 2008 | (CH) | 0863/08 |
| Mar. 19, 2009 | (CH) | 0422/09 |

(51) Int. Cl.
*A61F 2/44*   (2006.01)
*A61F 2/46*   (2006.01)
*A61B 17/02*   (2006.01)
(Continued)

(52) U.S. Cl.
CPC ............ *A61F 2/4611* (2013.01); *A61F 2/447* (2013.01); *A61F 2/4455* (2013.01); *A61B 2017/0256* (2013.01); *A61F 2002/2835* (2013.01); *A61F 2002/3082* (2013.01); *A61F 2002/30289* (2013.01); *A61F 2002/30785* (2013.01); *A61F 2002/30841* (2013.01); *A61F 2002/4475* (2013.01); *A61F 2002/4623* (2013.01); *A61F 2002/4624* (2013.01); *A61F 2002/4629* (2013.01); *A61F 2230/0091* (2013.01); *A61F 2250/0006* (2013.01)

(58) Field of Classification Search
CPC ..... A61F 2/447; A61F 2/4611; A61F 2/4455; A61F 2/4475; A61F 2017/0256; A61F 2017/0262
USPC ............ 623/17.11–17.16; 606/105, 246, 248, 606/90, 914, 99, 293, 249, 57, 58
See application file for complete search history.

(56) References Cited

U.S. PATENT DOCUMENTS

| 4,834,757 | A | * | 5/1989 | Brantigan | A61B 17/1604 623/17.11 |
| 5,425,772 | A | * | 6/1995 | Brantigan | A61F 2/447 606/247 |
| 5,443,514 | A | * | 8/1995 | Steffee | A61F 2/447 128/898 |

(Continued)

FOREIGN PATENT DOCUMENTS

| FR | 2764795 A1 * 12/1998 ............ A61F 2/4455 |
| WO | WO 99/60957   5/2002 |
| WO | WO 03/009786   2/2003 |

*Primary Examiner* — Zade Coley

(74) *Attorney, Agent, or Firm* — Galbreath Law Offices, P.C.; John A. Galbreath

(57) ABSTRACT

The invention relates to an intersomatic cage comprising a body (3) and a part (2) that is designed to dilate the intersomatic space between two vertebrae (8, 8') by rotating the cage so that the cage (1) can be inserted into the space. The body (3) has a prism shape with a substantially planar upper surface (6) which can bear against the superior vertebral endplate (8) and a substantially planar lower surface (6') which can bear against the inferior vertebral endplate (8').

12 Claims, 12 Drawing Sheets

(51) Int. Cl.
*A61F 2/28* (2006.01)
*A61F 2/30* (2006.01)

(56) References Cited

U.S. PATENT DOCUMENTS

| | | | | |
|---|---|---|---|---|
| 5,554,191 A * | 9/1996 | Lahille | ............... | A61B 17/1757 411/55 |
| 6,045,580 A * | 4/2000 | Scarborough | ...... | A61B 17/1637 606/247 |
| 6,290,724 B1 * | 9/2001 | Marino | ................ | A61F 2/4455 623/17.11 |
| 6,368,325 B1 * | 4/2002 | McKinley | ............ | A61F 2/4455 606/99 |
| 2001/0034553 A1 * | 10/2001 | Michelson | ........... | A61F 2/4455 623/17.11 |
| 2002/0029082 A1 * | 3/2002 | Muhanna | ............. | A61F 2/4455 623/17.11 |
| 2002/0055745 A1 * | 5/2002 | McKinley | ............ | A61F 2/4455 606/99 |
| 2003/0050701 A1 * | 3/2003 | Michelson | ........... | A61F 2/4455 623/17.11 |
| 2003/0114931 A1 * | 6/2003 | Lee | ....................... | A61F 2/4455 623/17.11 |
| 2003/0135275 A1 * | 7/2003 | Garcia | ............... | A61B 17/1671 623/17.11 |
| 2003/0139812 A1 * | 7/2003 | Garcia | ............... | A61B 17/1671 623/17.11 |
| 2004/0106996 A1 * | 6/2004 | Liu | ...................... | A61B 17/025 623/17.11 |
| 2004/0267365 A1 * | 12/2004 | Fornari | ................... | A61F 2/446 623/17.16 |
| 2005/0049704 A1 * | 3/2005 | Jackson | ............. | A61B 17/7032 623/17.11 |
| 2006/0058878 A1 * | 3/2006 | Michelson | .............. | A61F 2/446 623/17.11 |
| 2006/0217806 A1 * | 9/2006 | Peterman | ............... | A61F 2/4455 623/17.11 |
| 2007/0282446 A1 * | 12/2007 | Li | .......................... | A61B 17/68 623/17.12 |
| 2008/0015701 A1 * | 1/2008 | Garcia | ................. | A61B 17/025 623/17.16 |
| 2008/0195209 A1 * | 8/2008 | Garcia | ............... | A61B 17/1671 623/17.16 |

* cited by examiner

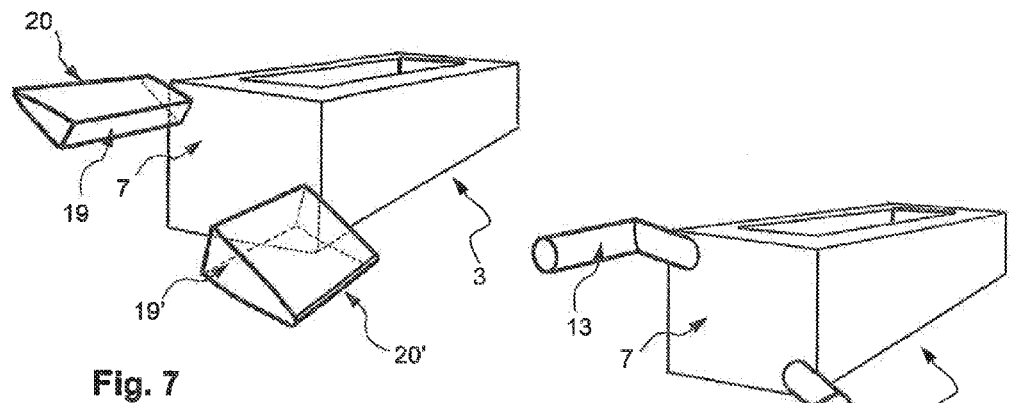
Fig. 7
Fig. 7a
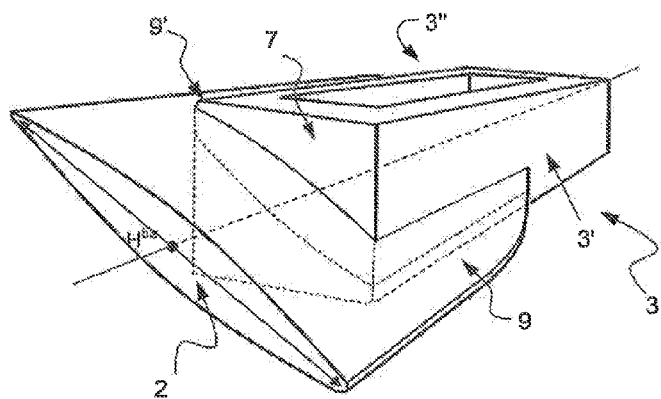
Fig. 8

INTERSOMATIC CAGE

The present invention relates to the medical field and more particularly to an intersomatic cage notably with an insertion tongue.

TECHNICAL FIELD

Certain pathologies of the spinal column, notably degenerative diseases of the disk and of the facets and vertebral dislocations, compromise the supporting capacity of the column and the distribution of load.

The treatments for these pathologies in their advanced stages make use of various stabilization systems by intradiscal implants of the intersomatic cage type, which may or may not be coupled to extradiscal implants which notably combine the use of vertebral screws and plates or rods.

These intradiscal implant systems have made it possible to very significantly improve the treatment of the pathologies of the spinal column by reestablishing the intervertebral space, which decompresses the nerve roots and accelerates the bony fusion of the adjacent vertebrae.

These intersomatic cages are of several types: the first category includes the threaded cages which are of essentially cylindrical shape and which are screwed into the intervertebral space. WO 03/009786 describes for example a cage of this type comprising an insertion tongue of rectangular, elliptical or oval shape situated at the front of the cage. The cross section of this tongue progressively increases along the longitudinal axis of the cage from its end to the threaded part of said cage, so as to allow the insertion of the latter into the intersomatic space and then the expansion of this space by the screwing of the cage.

The main drawback of these types of threaded cages lies in the fact that they do not make it possible to reproduce a lordosis angle close to the natural angle of the segment.

Impaction cages form the second category, in which the cage of mainly parallelepipedal shape is inserted between the vertebrae by the application of impacts. The drawback of these cages is the difficulty of inserting into the intersomatic space, by posterior approach, after partial laminectomies and facectomies, or else by transforaminal or lateral approaches, cages comprising a cross section of considerable height in order to treat the vertebral segments where the natural sagittal position is substantially lordotic, notably when the natural angle to be reestablished is greater than 10°. Systems of cages that can be expanded in situ have been developed to make it possible to obtain such heights in the anterior part of the cages, but often at the price of diminished solidity, strength and stability.

The object of the present invention is therefore to propose an intersomatic cage in a single homogeneous body the geometry of which has the merit of remedying these drawbacks.

Another object of the present invention is to propose a device for inserting the intersomatic cage into the intervertebral space.

According to the invention, this object is achieved by virtue of an intersomatic cage comprising a body and a part designed to expand the intersomatic space between two vertebrae by rotating the cage in order to be able to insert said cage therein by the effect of a push. The body has a shape of a prism comprising an essentially flat superior surface suitable for pressing against the plate of the superior vertebra and an essentially flat inferior surface suitable for pressing against the plate of the inferior vertebra.

The advantage of the present invention lies in the fact that it allows the insertion of cages comprising a cross section of considerable height and of which the superior and inferior faces are inclined, notably toward the rear of the cage in order to offer a lordosis angle close to the natural angle of the segment which may be substantially greater than 10°, which is not possible for threaded cages inserted by posterior approach as described in WO03/009896.

Moreover, compared with the prior art, the invention also makes it possible to insert a cage in parallelepipedal shape or of a trapezoidal cross section into the intervertebral space without necessarily having to use impaction to insert the body of the cage, a pressure sufficient for its insertion.

The features of the invention will appear more clearly on reading a description of several embodiments given only as examples that are in no way limiting, with reference to the schematic figures in which:

FIG. 7 represents a view in perspective of a cage with two flaps according to a seventh embodiment;

FIG. 7a represents a view in perspective of a cage with two bent rods according to one variant embodiment;

FIG. 8 represents a front view in perspective of a cage comprising an insertion tongue in an oblique plane and lateral wings on a part of the body of the cage according to a ninth embodiment;

FIG. 10c represents a front view of FIG. 10a;

FIG. 14c represents a detailed view in perspective of FIG. 14a.

EMBODIMENT OF THE INVENTION

In the following description of the various intersomatic cages, reference is made notably to the horizontal plane of the cage that will be assumed to be in a plane parallel to the axial or transverse plane of the human body, this horizontal plane corresponding to the position of the cage in its length when the latter is in its final position between two vertebrae.

Figure 1:
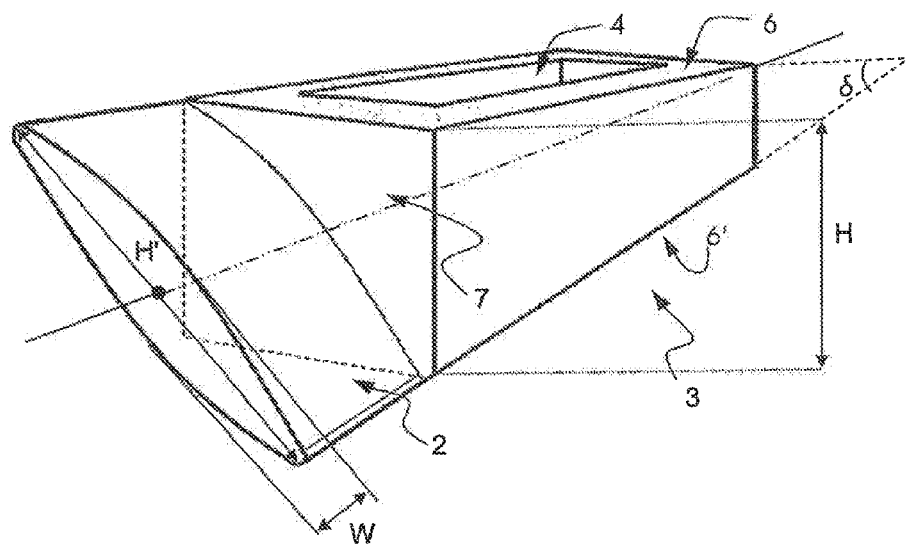
FIG. 1 represents a front view in perspective of a cage comprising an insertion tongue oriented on a plane inclined at approximately 45° relative to the horizontal plane of the cage according to a first embodiment.

According to the first embodiment of the invention, FIG. 1 illustrates an intersomatic cage for posterior/postero-lateral approaches. This cage comprises a body 3 with a conventional shape of an impaction cage, namely essentially parallelepipedal or a body 3 having a longitudinal section of trapezoidal shape. This body 3 has a superior and inferior surface 6, 6' designed to come into contact with the respective superior and inferior vertebral plates. These two surfaces 6, 6' are inclined relative to a horizontal plane so as to obtain a body 3 in which the height of the anterior side 7 is greater than the height of the posterior side (not visible). These two surfaces 6, 6' have between them an angle 5 ranging typically from 4° to 15°, or even greater, to allow the vertebrae of the segment to be placed in lordosis. These surfaces 6, 6' may be covered with crenellations to prevent the cage from migrating forward or rearward. Moreover, the body of the cage may comprise a through recess in the height direction so as to allow the stuffing of grafts promoting the bony fusion between the two adjacent vertebrae.

This cage also comprises a part 2 designed to expand the intersomatic space between two vertebrae for the insertion of the intersomatic cage. The part 2, which in this instance will more commonly be called the insertion tongue, has a substantially oblong shape with a height H' and width W. This part 2 is arranged perpendicularly on the anterior side 7 of the cage body 3 and in an inclined plane forming an angle of approximately 45° with the horizontal plane of the cage so that said part 2 extends in the direction of its height H' along the diagonal of the anterior side 7 of the cage body 3.

Figure 1A:
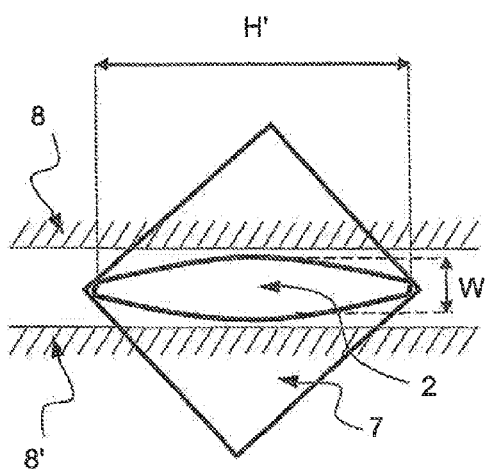
FIG. 1a represents a front view of FIG. 1 when the tongue is inserted into the slightly expanded intersomatic space.
Figure 1B:
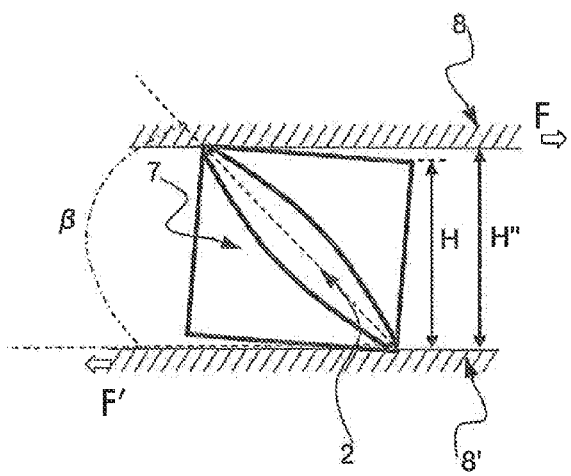
FIG. 1b represents a front view of FIG. 1 after rotation of the cage through approximately 45° and full expansion of the intersomatic space.

It goes without saying that the incline of the tongue 2 may vary on an oblique plane comprising an angle of preferably between 40° and 60° relative to the horizontal plane of the cage. According to FIG. 1, the height H' of the tongue 2 is greater than the height of the highest section H of the body 3. According to FIGS. 1a and 1b, it is noted that the dimensions of the tongue 2 make it possible to significantly reduce the angle of rotation necessary to expand the intersomatic space between the vertebrae 8, 8' in order to insert the whole of the cage body 3. Specifically, according to FIG. 1b, the intersomatic space of height H" which is greater than the height H of the body 3 in its anterior part is obtained by a rotation through an angle β close to 45°. This makes it possible to significantly reduce the shearing stress forces F, F' exerted between them by the two vertebrae 8, 8' of the segment. The angle of rotation may also be greater than that necessary to obtain the height H", notably in order to ensure that cages comprising surfaces with high crenellations pass. The lateral flanks of the tongue 2 make it possible to insert and guide the body 3 pressing against the two respective vertebral plates 8, 8' along a plane inclined at the angle β in the intersomatic space before said body 3 reaches its final position and performs a slight contra-rotation under the effect of the compression of the vertebrae 8, 8'.

For the insertion of the cage, an instrument may be screwed on the posterior side of the body 3. After the extraction of all or some of the intervertebral disk, and if necessary after application of dilation candles in the intersomatic space, then moving the nerve roots aside, the cage is implanted in five steps, namely: insertion of the cage into the rachidian canal; rotation; insertion/pressing of the insertion tongue 2 into the intervertebral space; contra-rotation; pushing the cage into the intervertebral space. More precisely, the implantation steps are as follows:

insertion of the cage into the rachidian canal with its insertion tongue 2 in the vertical position. When the front of the insertion tongue 2 makes contact with the vertebrae, the cage is turned through an angle substantially less than 90° in order to tilt the insertion tongue 2 to the horizontal which allows it to be inserted into the slightly expanded intervertebral space. The cage is then again turned through an angle of less than 90°, but in the opposite direction to the second step, which has the effect of expanding the intervertebral space to a height close to the height H' of the insertion tongue 2 of the cage. The latter is then pushed or, if necessary, impacted, into the intervertebral space to its final position. The insertion tongue can be made of a different material from that of the body, for example resorbable material designed to disappear in order to leave room for the bony growth, or an osteoconductive material designed to promote said bony growth.

Figure 2:
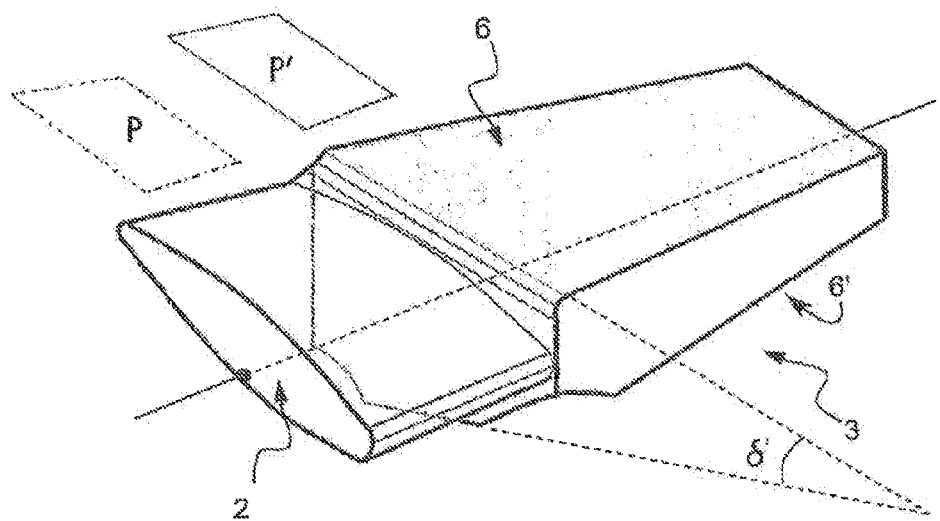
FIG. 2 represents a front view in perspective of a cage with lateral asymmetry for a unilateral, transforaminal or lateral approaches, with central insertion tongue in an oblique plane parallel to the superior surface of the cage according to a second embodiment.

FIG. 2, according to the second embodiment of the invention, represents an intersomatic cage for unilateral, transforaminal or lateral approaches, that is to say a cage which is inserted in a posterolateral or lateral manner, and of which the final positioning is situated in the anterior part of the intersomatic space, perpendicular to the sagittal plane. The instrumentation of an intervertebral segment with such a cage does not in principle require the insertion of a second cage. The particular feature of this cage lies in the fact that it comprises a cage body 3 which is asymmetrical not lengthwise (as described in the first embodiment) but widthwise. The lordosis angle 5' that is sought for the final position of the vertebrae of the segment is given, in this case, by the angle obtained by the extension of the superior and inferior surfaces 6, 6' widthwise. According to FIG. 2, the cage comprises an insertion tongue 2 which is in a plane P parallel to a plane P' containing the superior surface 6 of the cage body 3. The tongue 2 is off-center in a plane parallel to a horizontal plane halfway up the cage body 3.

Figure 2A:
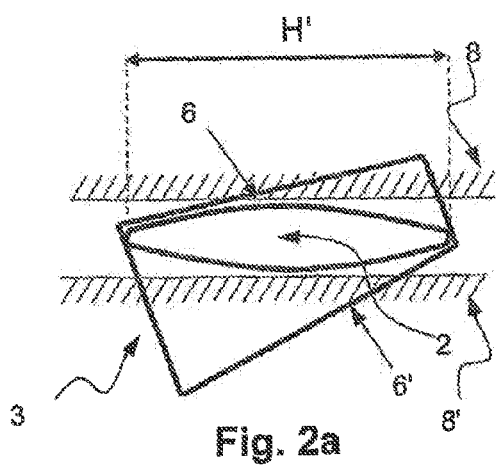
FIG. 2a represents a front view of a cage with lateral asymmetry according to one variant embodiment with the insertion tongue inserted into the slightly expanded intersomatic space.
Figure 2B:
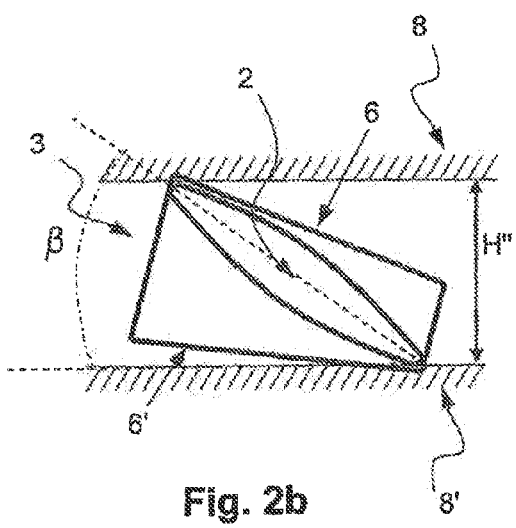
FIG. 2b represents a front view of the cage according to this variant after rotation of said cage through an angle of less than 45°.

In a variant shown by FIGS. 2a and 2b, the tongue 2 is in an oblique plane relative to the plane containing the superior or inferior surface of the body 3. This makes it possible to lengthen the height H' of the insertion tongue 2 which, in its turn, reduces the angle of rotation β necessary for the sufficient expansion of the intersomatic space H" in order to ensure that the body 3 of the cage passes. This angle accordingly reduces the shearing stress forces exerted between the vertebrae 8, 8' of the segment, which may promote the maintenance of the trajectories of the implant into the intersomatic space.

When the insertion tongue 2 first makes contact against the vertebrae 8, 8' (FIG. 2a), the tongue is, if necessary, inserted directly without prior rotation into the preexpanded intersomatic space or, if necessary, after a slight rotation impressed upon the cage in order to align the tongue 2 in the plane of the intersomatic space. After the tongue 2 has been fully inserted, a rotation through approximately 45° is carried out (FIG. 2b) which has the effect of expanding the space by a height H" that is sufficient to ensure that the body 3 with its highest cross section passes between the superior and inferior faces 6, 6'. The cage is then pushed or, if necessary, impacted, until the body 3 fully enters the intersomatic space and is pushed into its final position, in the anterior part of said space. Although according to FIG. 2b the angle of rotation β is approximately 45°, it may be smaller or greater depending on the ratio between the height and the width of the cage (for example between 30° and 60°). This cage may also be arched relative to its longitudinal axis in order to conform to the shape of the anatomy of the vertebral body in its anterior part.

Figure 3:
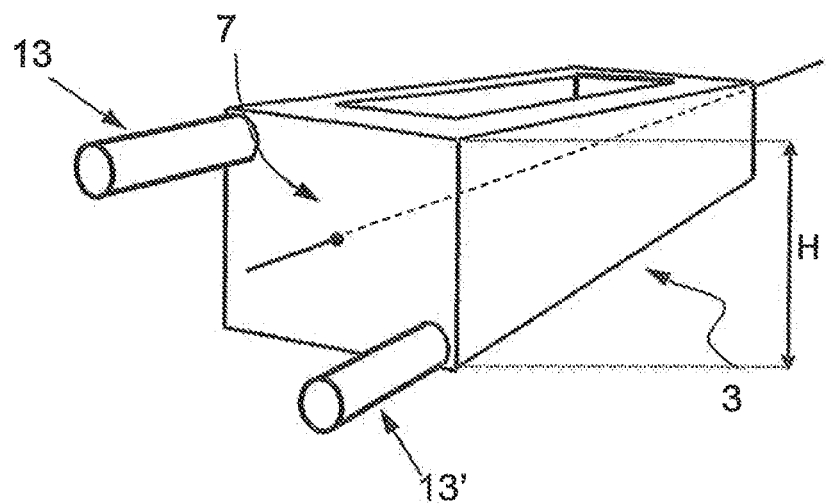
FIG. 3 represents a view in perspective of a cage comprising two insertion rods according to a third embodiment.

According to a third embodiment of the invention, FIG. 3 represents an intersomatic cage which comprises a cage body 3 with a geometric shape similar to the cage body of the first two embodiments. Two rods 13, 13' are mounted on the anterior side 7 of the body 3 in two diagonally opposite corners. These two rods 13, 13' are oriented on an axis perpendicular to the anterior side 7 and have sufficient length to be able to be inserted far enough forward between two adjacent vertebrae and serve as lever arms for expanding the space by a rotary movement. Preferably, this length is between 6 and 7 mm. The arrangement of these rods 13, 13' makes it possible to obtain a technical effect similar to that obtained by the insertion tongue 2 according to the first embodiment when the cage is inserted into the intervertebral space.

This cage is inserted through the rachidian canal on a horizontal plane of the body 3, or else, if it is desired that the rods 13, 13' return to a vertical plane (for example in order to bypass the nerve roots) the body must be tilted in a plane between 40° and 60° depending on the height-width ratio of the anterior side 7 of the cage body 3. When the rods 13, 13' touch one or both vertebrae of a segment, the cage is then tilted until the rods 13, 13' are again in a horizontal plane (the body of the cage then being in an oblique plane between 40° and 60° depending on the height-width ratio of the anterior side 7 of the body).

According to a variant, the two rods can be arranged relative to one another so as to return to a vertical plane, horizontal plane or else to an oblique plane forming an angle different from 45° with the horizontal plane of the cage. The plane will be chosen depending on the desire to limit or increase the angle of rotation and the force necessary for the sufficient expansion of the intersomatic space for the insertion of the body 3. The plane may pass over the longitudinal median axis of the body of the cage or be situated beside said axis, in order to increase or attenuate the cam effect of the body at the time of its rotation, of one or other of its sides. One or more median rods between the two rods may be added. The cross section of the rods may naturally be of any shape, notably square, oval or oblong.

Figure 4:
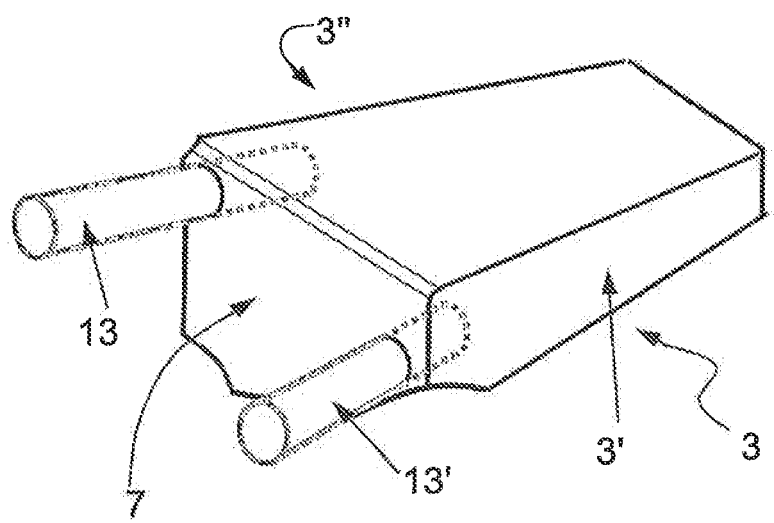
FIG. 4 represents a view in perspective of a cage with lateral asymmetry for transforaminal or lateral approaches with two insertion rods according to a fourth embodiment.

According to a fourth embodiment of the invention, FIG. 4 represents a cage which differs from the cage according to the previous embodiment in the geometric shape of the body 3 which is suitable for transforaminal or lateral approaches, that is to say that it is a cage designed to be positioned laterally in the intersomatic space. The body 3 of this cage has a geometric shape similar to that of the second embodiment (FIG. 2) and therefore has a lateral side 3" that is higher than the other (3'), while its anterior side 7 and posterior side (not visible) are of similar height. The rods 13, 13' are mounted on the anterior side 7 of the cage body 3. These rods 13, 13' may form an integral part of the body, or they may be fitted, crimped or screwed into said body by one of their ends. These rods may be made of a material different from that of the body, for example a resorbable material designed to disappear in order to leave room for the bony growth, or an osteoconductive material designed to promote said bony growth.

Figure 5:
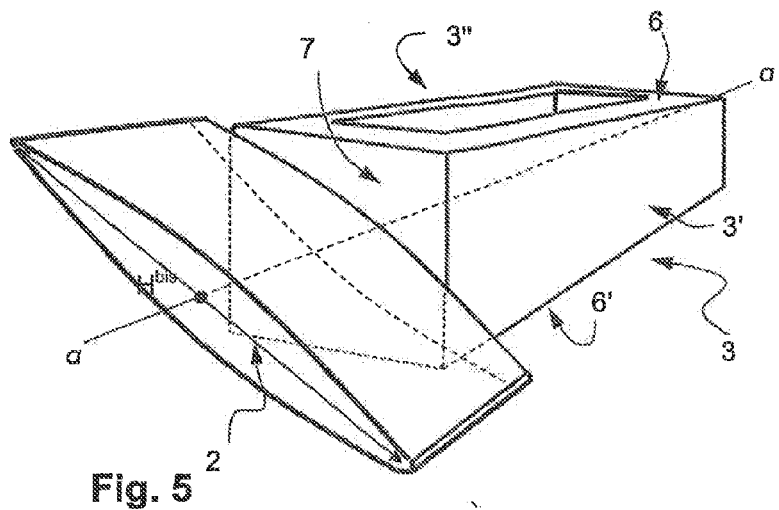
FIG. 5 represents a view in perspective of a cage with an insertion tongue the lateral flanks of which are situated beyond the lateral sides of the cage body according to a fifth embodiment.

According to a fifth embodiment, FIG. 5 represents an intersomatic cage for posterior/posterolateral approaches which comprise, on the one hand, a cage body with a geometric shape preferably identical or similar to the cage body according to the first embodiment and, on the other hand, a part 2 designed to expand the intersomatic space. This part 2, which will also be called the insertion tongue, is arranged on the anterior side 7 of the body 3 of the cage. This tongue 2 extends beyond the lateral sides of this body 3', 3", so that the height $H^{bis}$ of the tongue 2 is greater than the diagonal of the anterior side 7. The increased dimensions of this tongue 2 make it possible to reduce the angle of rotation necessary for the expansion of the intersomatic space. In other words, this tongue 2 reduces the necessary torsional force and the cam effect of the body. The lateral edges of the tongue 2 are not necessarily parallel but preferably they do not protrude relative to the superior and inferior faces 6, 6' of the cage body 3 once the cage is in its final position so as not to interfere with the contact of said faces with their respective vertebral plate.

Figure 5A:
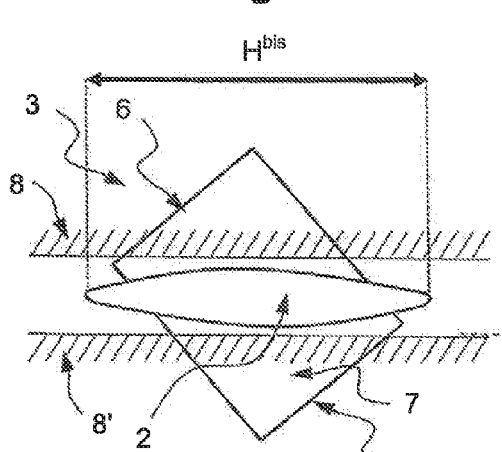
FIG. 5a represents a front view of FIG. 5 when the insertion tongue is inserted into the slightly expanded intersomatic space.
Figure 5B:
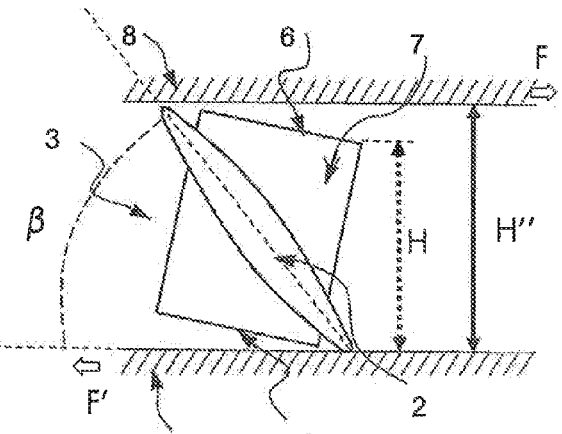
FIG. 5b represents a front view of FIG. 5 after rotation of the cage through an angle β.

FIG. 5a represents the intersomatic cage just before a rotation is impressed on the body 3 when the insertion tongue 2 is horizontal in the intersomatic space between the vertebrae 8, 8'. FIG. 5b illustrates the end of the rotation of the cage through an angle β, with the intersomatic space expanded to a height H" sufficient to be able to push the whole of the body 3 of the cage into the intersomatic space without the surfaces 6, 6' rubbing the vertebral plates 8, 8'. Specifically, the height H of the cage with its highest cross section is much smaller than the height H" of the intervertebral space necessary for the body 3 to pass. This height difference makes it possible to reduce as much as possible the angle β, and consequently the effect of the shearing stress forces F, F', the distraction force necessary for the expansion, and the cam effect of the body at the time of the rotation. FIG. 5b shows that the expansion of the intervertebral space has been obtained by a rotation through an angle β close to 45°, while the height of the body 3 is significantly greater than its width. This figure also shows that it is possible to apply profiles of considerable crenellations on the surfaces 6, 6' without the latter hampering the insertion of the cage.

Figure 6:
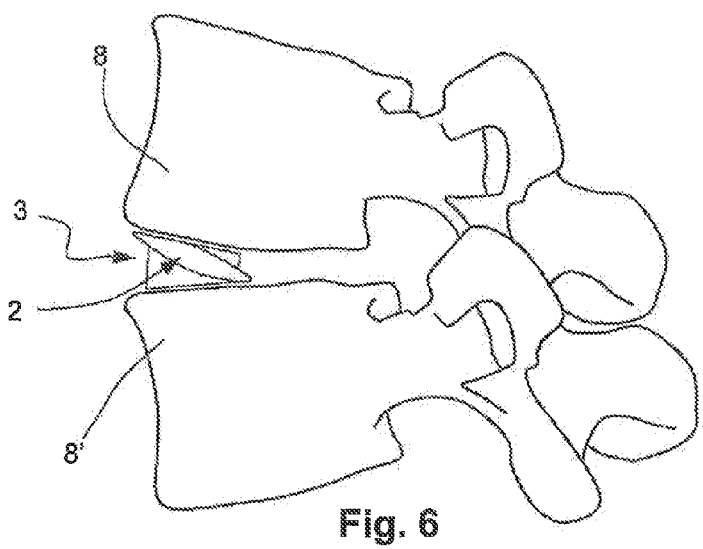
FIG. 6 represents a side view of two adjacent vertebrae and of a cage with lateral asymmetry adapted for transforaminal or lateral approaches according to a sixth embodiment.

According to a sixth embodiment, FIG. 6 represents a cage, for unilateral, transforaminal or lateral approaches, said cage being in its final position between two vertebrae 8, 8'. This cage comprises an insertion tongue 2 arranged on the anterior side 7 of a cage body 3 with a geometric shape similar to the cage body of the second embodiment. The particular feature of this cage lies in the fact that, unlike the second embodiment, the tongue 2 extends beyond the lateral sides of the body 3 so as to obtain the advantages described in the fifth embodiment not for a posterior/posterolateral approach but for unilateral, transforaminal and lateral approaches.

According to a seventh embodiment, FIG. 7 represents an intersomatic cage for posterior/posterolateral approaches comprising a cage body 3 with a geometric shape that is preferably identical or similar to the cage body according to the first embodiment and two flaps 19, 19' of trapezoidal cross section placed on the anterior side 7 of the body 3 and oriented in a plane corresponding to that of the insertion tongue according to the previous embodiment. The flaps 19, 19' are respectively arranged close to a first and second corner of the anterior side 7 said corners being diagonally opposite. These flaps 19, 19' comprise lateral flanks 20, 20' protruding beyond the edges of the anterior side 7 of the cage body 3. A variant as illustrated by FIG. 7a consists in substituting for the flaps two rods 13, 13' comprising a first segment that is oblique relative to the longitudinal axis of the body 3, and a second rectilinear segment oriented on another axis in order that a part of the rods 13, 13' are situated outside the vertical plane coinciding with the two lateral sides of the body 3.

According to an eighth embodiment, FIG. 8 illustrates an intersomatic cage similar to the cage described in the fifth embodiment except that this cage also comprises, in the extension of the tongue 2, a wing 9, 9' arranged along each of the two lateral sides 3', 3" of the cage body 3. The height $H^{bis}$ of the tongue 2 is substantially greater than the height of the body 3 at its highest section, namely at its anterior side 7. It goes without saying that the shape of the wings 9, 9' and their dimensions can be arbitrary. For example, the width of the wings 9, 9' may increase or decrease along the longitudinal axis of the cage and/or extend over the whole length of the lateral sides 3', 3" of the body 3. The wings may also be noncontinuous and therefore consist of several segments along the lateral sides.

Figure 8A:
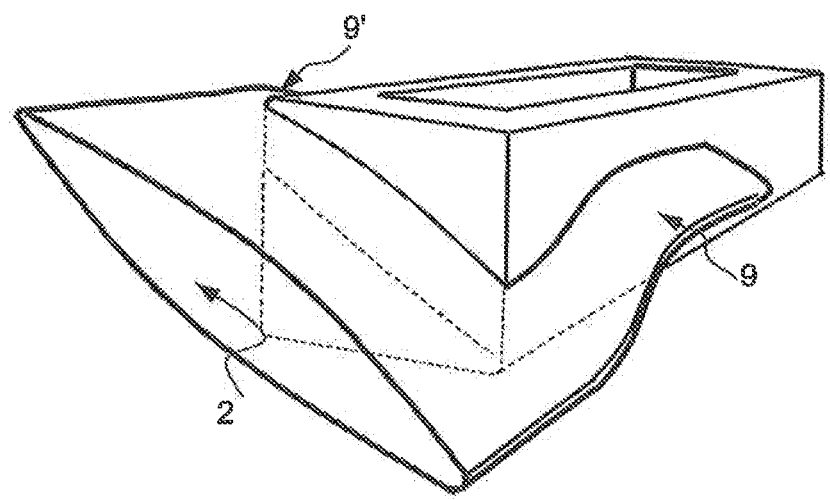
FIG. 8a represents a view similar to FIG. 8 but with curved wings according to a first variant embodiment.

Another example is illustrated by FIG. 8a which represents a cage comprising curved wings 9, 9' so as to promote the changes of trajectory in the intersomatic space and thus improve the final positioning of said cage. According to a variant not shown, these wings 9, 9' may also display a rectilinear shape inclined at any angle along the lateral sides, an angle that differs from the plane formed by the tongue 2.

Figure 8B:
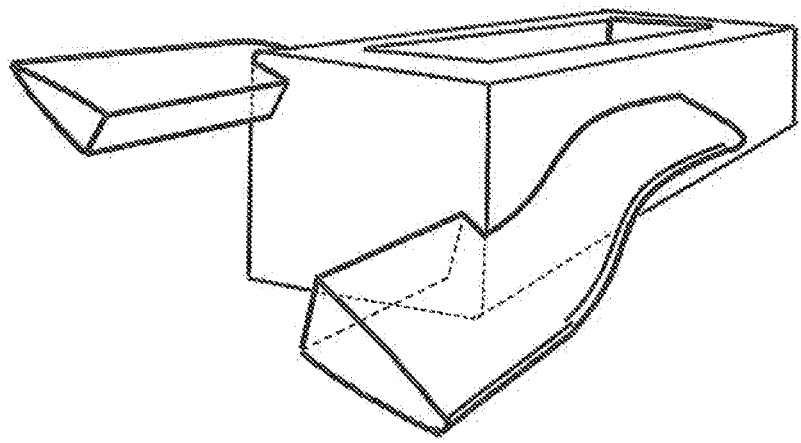
FIG. 8b represents a view in perspective of a cage with two opposite flaps protruding from the lateral sides of the body and extending along said sides according to a second variant embodiment.

According to another example as shown by FIG. 8b, the cage comprises an insertion tongue combining certain features of the intersomatic cages illustrated in FIGS. 7 and 8a.

Figure 9A:
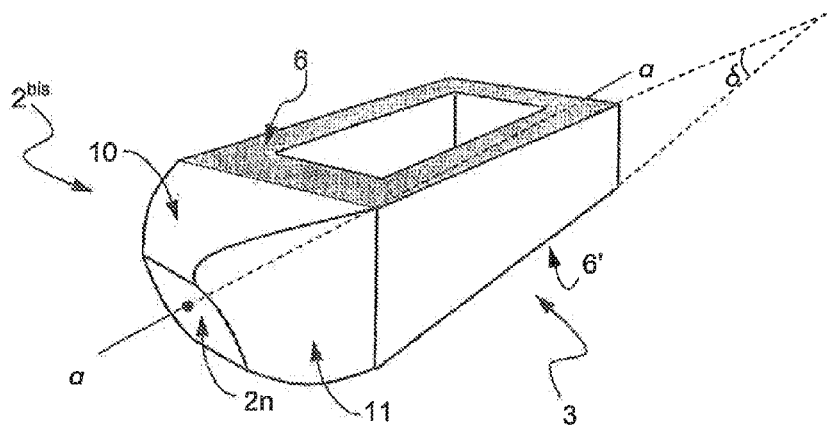
FIG. 9a represents a front view in perspective of a cage the end of which comprises two surfaces having a slope of helical gradient according to a 9th embodiment.

According to a ninth embodiment of the invention, FIG. 9a represents an intersomatic cage for posterior/posterolateral approach comprising a body 3 and a part $2^{bis}$ designed to expand the intersomatic space between two vertebrae for the insertion of the cage. The superior and inferior faces 6, 6' of the body 3 are not parallel but positioned at an angle 5. This angle varies depending on the cages and is suitable for the lordotic angle desired depending on the vertebral segment that is instrumented. This angle may range typically from 4° to 15°, and even greater. The body may also have parallel superior and inferior surfaces. The part $2^{bis}$ is in the extension of the body 3 and comprises on the one hand a superior and inferior face 10, 10' (FIG. 9b) designed to come into contact with the respectively superior and inferior vertebra of the intersomatic space and on the other hand two lateral faces 11, 11'. These faces 10, 10', 11 and 11' converge from the respective edges of the anterior side of the body 3 up to a flat face $2n$ centered halfway up and halfway across said anterior side. This central face $2n$ has a shape similar to an insertion tongue as described in certain of the previous embodiments but with much smaller dimensions than the dimensions of the cage body 3. This flat face $2n$ stretches in the direction of the diagonal of the anterior side so as to form an angle β with the horizontal plane of the cage 3. The faces 10, 10' are identical and are inclined and curved so as to reproduce the beginning of a slope with a helical gradient in order to be able to transmit a rotation of the body 3 simply by pressing on the posterior part of said body 3 when the central part $2n$ is arranged in the intersomatic space.

Figure 9B:
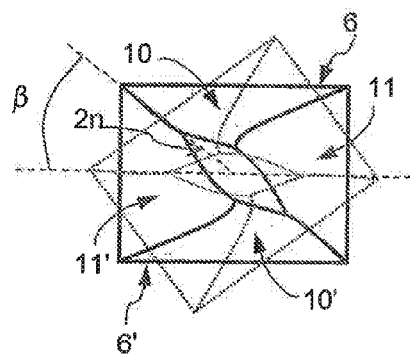
FIG. 9b represents a front view of FIG. 9a when the cage is in its final position with, in faint line, the position of the cage at the moment of engagement of its end in the intersomatic space.

According to FIG. 9b, the cage illustrated in faint line represents the latter when the flat surface $2n$ is arranged in correspondence with the intersomatic space just before the insertion of the end of the part $2^{bis}$ into the intersomatic space. At this moment, the cage body 3 is inclined by approximately 45° relative to the vertebral plates and the surfaces 10, 10' are in contact with the latter. When a pressure is exerted at the back of the body 3, the latter begins to rotate by virtue of the profiles of the surfaces 10, 10' until it is again in the horizontal plane of the cage.

Figure 9C:
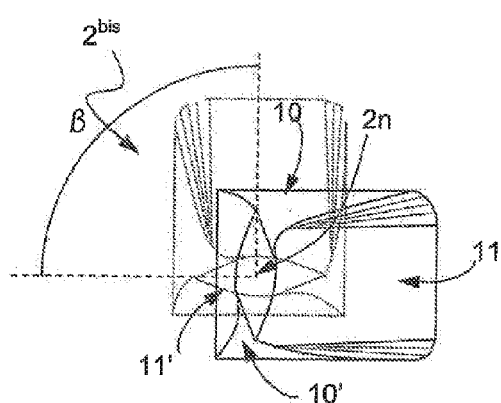
FIG. 9c represents a front view of a cage according to a first embodiment, when the cage is in its final position with, in faint line, the position of the cage at the moment of engagement of its end in the intersomatic space.

According to a first variant embodiment, FIG. 9c illustrates a cage similar to that represented in FIGS. 9a and 9b but in which the part $2^{bis}$ extends along a longitudinal axis that is off-center from the median longitudinal axis of the body 3 so that the surface $2n$ stretches along a vertical axis. FIG. 9c represents in heavy lines the final position of the cage and in faint line its position of engagement of the cage 3. The insertion of the end of the part $2^{bis}$ into the intersomatic space will in this instance cause an autorotational movement of the order of 90°.

Figure 9D:
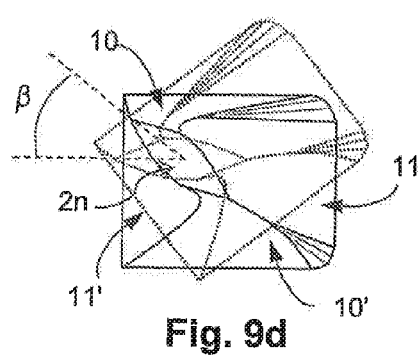
FIG. 9d represents a front view of a cage according to a second variant embodiment, when the cage is in its final position with, in faint line, the position of the cage at the moment of engagement of its end in the intersomatic space.

According to a second variant embodiment, FIG. 9d represents a cage in which the part $2^{bis}$ extends in a longitudinal axis that is off-center from the median longitudinal axis of the body so that the surface $2n$ stretches along an axis inclined at an angle β corresponding to 45°. The insertion of the end of the part $2^{bis}$ will in this instance cause an autorotational movement of the order of 45° but with a more pronounced cam effect on one side of the body 3 than the other.

Moreover, it goes without saying that the part $2^{bis}$ may be situated not on the anterior side but on one of the lateral sides of the cage body for transforaminal or lateral approaches.

Figure 10A:
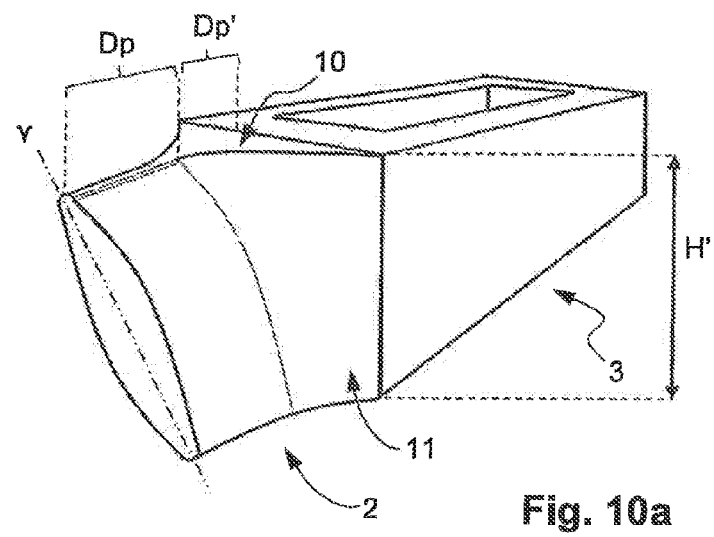
FIG. 10a represents a right front view in perspective of a hybrid cage according to a 10th embodiment.
Figure 10B:
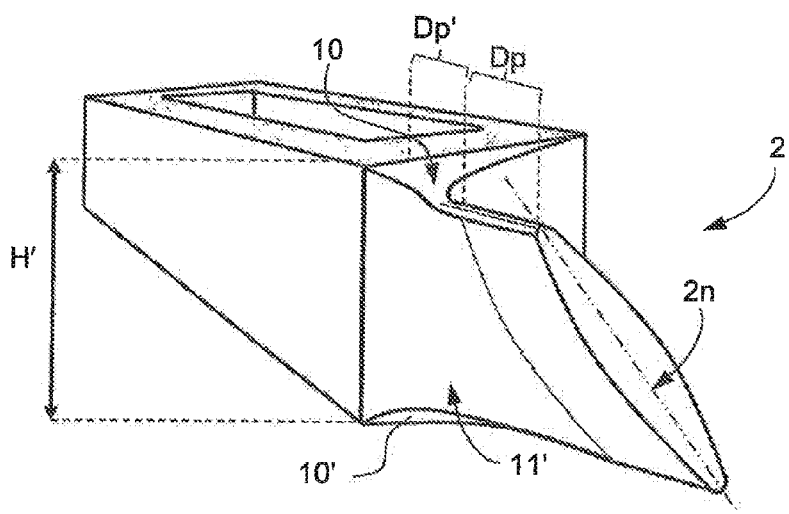
FIG. 10b represents the same cage as in FIG. 10a but in left front perspective.
Figure 10C:
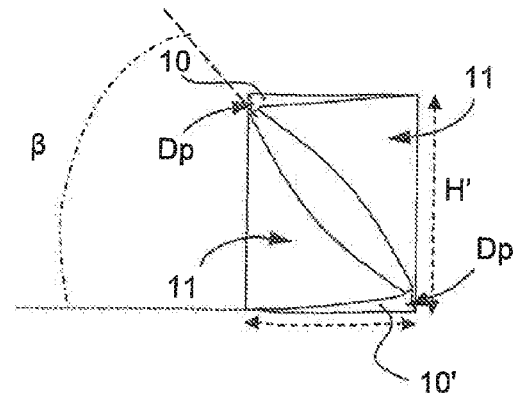

FIGS. 10a to 10c represent an intersomatic cage according to a 10th embodiment of the invention. This cage combines certain features of the previous embodiment with, in particular, the first embodiment. More precisely, the cage comprises on the one hand an insertion tongue 2 of depth Dp requiring an intentional rotational movement of the surgeon, and on the other hand an intermediate part of depth Dp' and arranged between the insertion tongue 2 and the anterior side of the cage body 3. This intermediate part comprises two lateral surfaces 11, 11' that are profiled so as to orient the tongue 2 into an inclined position relative to the horizontal plane of the cage at an angle β(FIG. 11c). Moreover, the superior and inferior surfaces 10, 10' (FIG. 11b) of said intermediate part are inclined and curved so as to reproduce the beginning of a slope with a helical gradient. The advantage of this cage is that it obtains a partial expansion of the intersomatic space through a slight rotation in order to be able subsequently to push the cage and cause the autorotational effect by virtue of the intermediate part with a much weaker pressure than the pressure that would have to be applied to a cage similar to that illustrated in FIG. 9a. This combination also has the advantage over a cage as described in the first embodiment, because of the presence of a twisting component, of requiring no more than a small angle of rotation which reduces the shearing stress forces between the two adjacent vertebrae. Specifically, when these forces are too strong, they are likely to cause the cage to "slip sideways" at the moment of the final push and thus cause it to come out of the desired trajectory. Finally, the height of the insertion tongue 2 may be less than the height H of the cage body 3 which may be an advantage to avoid the hard or soft tissues at the moment of insertion through the rachidian canal.

In order to insert this cage, the insertion tongue 2 is oriented in correspondence with the intersomatic space and is then inserted between the vertebral plates. A rotation of substantially less than 90° is impressed by the surgeon in order to partly expand the intersomatic space and then, before this space is as high as the height of the body 3, the cage is pushed forward, and the intermediate part takes over and continues the expansion of the intersomatic space according to the autorotational principle, without any other intentional rotation being necessary on the part of the surgeon. In a variant (not shown), the part designed to expand the intersomatic space is situated on one of the lateral sides of a cage body with lateral asymmetry for transforaminal or lateral approaches.

Another variant (not shown) consists in combining the features of the anterior part of a cage with slopes with a helical gradient of the ninth embodiment, with, for example, the lateral wings of the eighth embodiment. This hybrid cage operates in the reverse manner to the hybrid cage of the 10th embodiment in that the cage is initially inserted by pushing or impaction into the intersomatic space via its part with slopes of helical gradient, which initiates an autorotation movement and slightly expands the intervertebral space, then, once the wings are engaged in the intersomatic space to a sufficient depth, the surgeon exerts an intentional rotation to complete the expansion to a sufficient height to cause the body of the cage to enter fully simply by pushing. A variant embodiment consists in replacing the anterior part with slopes of a helical gradient with an anterior face of the body having a round or ogival profile helping the initial push or impaction.

Figure 11A:
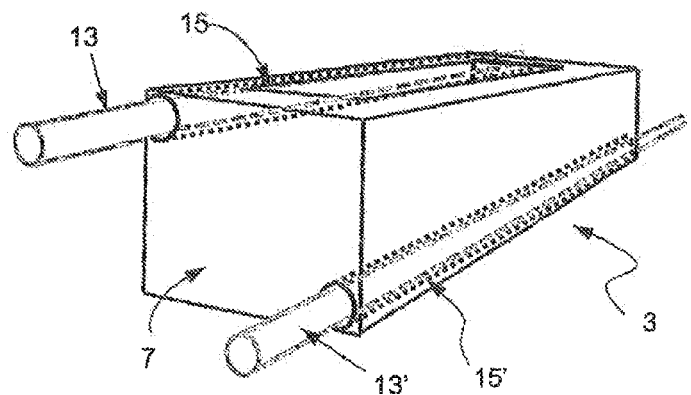
FIG. 11a represents a view in perspective of an intersomatic cage with two removable insertion rods according to an 11th embodiment.
Figure 11B:
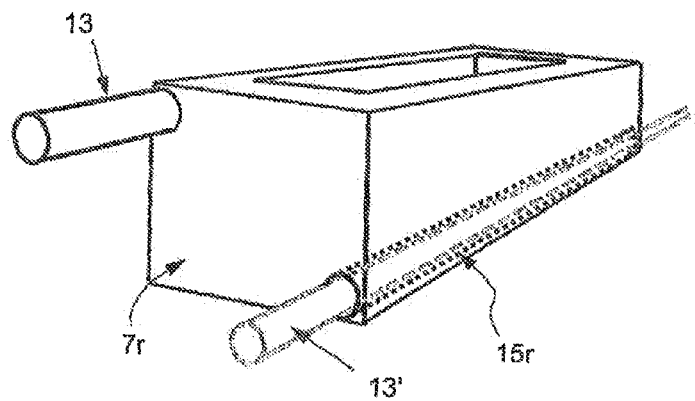
FIG. 11b represents a view in perspective of an intersomatic cage according to a first embodiment.
Figure 11C:
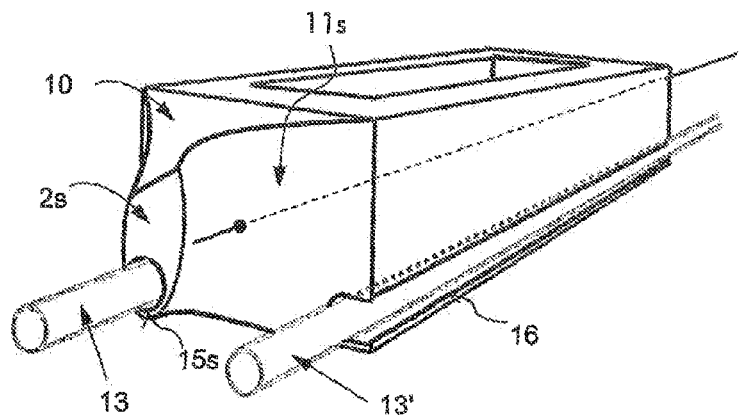
FIG. 11c represents a view in perspective of a hybrid intersomatic cage according to a second variant embodiment.

According to an 11th embodiment as illustrated by FIG. 11a, the expansion of the intersomatic space between two vertebrae is achieved by two rods 13, 13' forming an integral part of an ancillary placement element of the cage. The advantage of this embodiment over the third embodiment is that it makes it possible to eliminate the space requirement formed by the rods in the intersomatic space. Two longitudinal runners 15, 15', designed to receive the rods 13, 13', pass through the cage body 3 from end to end. More precisely, these runners 15, 15' are arranged along two distinct longitudinal axes perpendicular to the anterior side 7 of said body 3 and situated in two diagonally opposite corners of said side 7. The rods may also be oriented in an axis not parallel to one of the lateral sides of the body. In order to ensure the stability of these rods 13, 13', they may be attached to the body 3 in a temporary manner, for example at the height of the posterior part of said body 3 or by an attachment (by screwing or other fastening means) to the ancillary placement element (not shown) of the cage. The rods 13, 13' may already be in position as shown in FIG. 11a or may be slid, after the insertion of the cage and its passage into the rachidian canal. The rods 13, 13' can be withdrawn after the rotation of the cage body 3 and before it is pushed into the intersomatic space, or else after said push, when the cage is in its final position. FIG. 11b represents a variant in which only one of the rods 13, 13' is removable, the other forming an integral part of the cage body 3. This variant may be advantageous for reducing the space requirement of the intersomatic space to only a single rod, while providing stability to the lever arm formed by the two rods 13, 13'.

FIG. 11c introduces a second variant in which the cage comprises a cage body 3 and a part 11 arranged on the anterior side of the body 3. This part 11 has a superior surface 10 and inferior surface (not visible) which are inclined so as to reproduce the beginning of a slope with a helical gradient. This cage makes it possible to obtain an effect comparable to that obtained by the cage according to the 10th embodiment when it is inserted into the intersomatic space, namely a partial expansion of this space by a slight rotation of the ancillary placement element (not illustrated) in order to be able subsequently to push the cage and cause the autorotational effect by virtue of the profile of the superior and inferior surfaces of the part 11. This cage in this instance incorporates two moveable rods 13, 13' arranged in a horizontal plane parallel with a mid-plane of the cage body 3. One of the rods (13) is arranged in a longitudinal runner 15 so that its end protrudes in the extension of the part 11 which comprises a truncated end 2 while the other rod 13' is arranged in a runner or a longitudinal groove 16. After the rods 13, 13' are inserted into the intervertebral space, a rotary movement is impressed on the ancillary placement element so as to raise the rod 13. This movement may be slight (less than 45°) because it simply has to allow the engagement of the truncated end 2 of the part 11 in the half-expanded intervertebral space (the body 3 also being in the same plane as the two rods 13, 13', namely less than 45°), before a push or an impact on the posterior part of the body 3 causes the additional rotation necessary for the expansion of the intersomatic space, to a sufficient height for the insertion of the body into said intervertebral space. The advantage of this variant is that, because of the small angle of rotation necessary for the lever effect, this reduces the cam effect induced by the rotation, which can be advantageous in the presence of nerves or hard tissues nearby. It is quite clear that the profile of the part 11, and mainly the superior surface 10 and inferior surface (not visible) can vary so as to provide the most ergonomic link to the superior face and/or inferior face of the body 3. Naturally, the insertion tongue 2 part with its depth Dp may be not only in a plane that is oblique relative to the horizontal plane along the horizontal plane of the cage, at an arbitrary angle, but may also be in a horizontal plane, namely indistinguishable from or parallel to the superior or inferior surfaces of the cage body.

Figure 12:
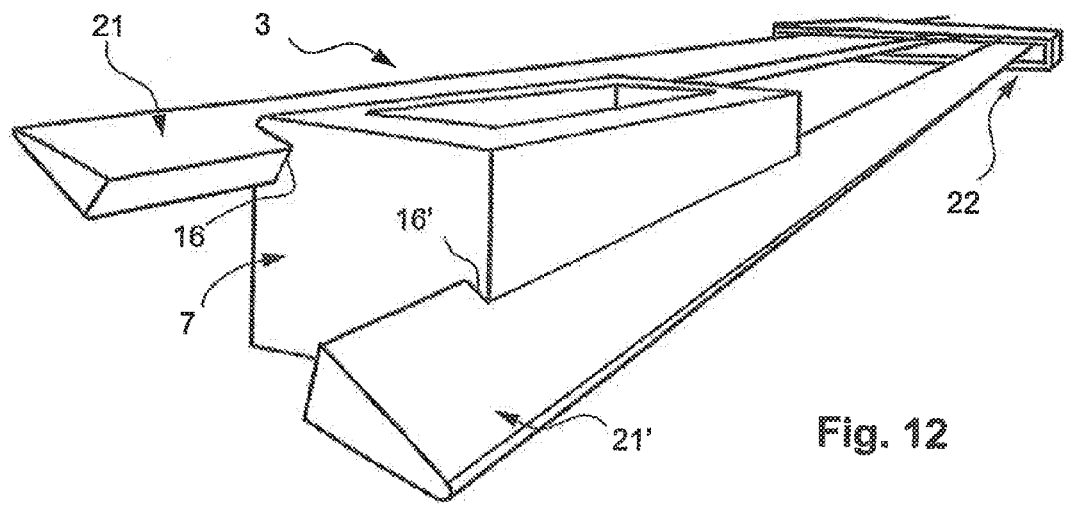
FIG. 12 represents a view in perspective of a cage with strips forming an integral part of an ancillary placement element according to a 12th embodiment.

According to a 12th embodiment, FIG. 12 represents a conventional cage consisting only of a body 3. This body 3 has, on each of its lateral sides, a groove 16, 16' oriented in the direction of the longitudinal axis of the cage. These grooves 16, 16' are designed to receive strips 21, 21' forming an integral part of an ancillary placement element, these strips having the function of expanding the intersomatic space between two vertebrae, according to the same principle as that described for the embodiment. In order to hold the strips inside the grooves, the latter preferably have a cross section of trapezoidal shape. Naturally, the strips may have a different section, notably oval or oblong, if they can be held inside their grooves 16, 16' by a mechanical means, for example at the ancillary placement element or by a member for connection between the strips at their anterior end protruding from the body 3. Note that the strips may be arranged not on the lateral sides of the body but on its superior and inferior surfaces, or even a configuration in which one strip has its groove in the superior surface or inferior surface of the body and the other strip has its groove in one of the lateral sides. Moreover, one of the strips may have a greater width than the other.

A variant embodiment (not shown) consists in combining a removable strip feature of this 12th embodiment with a wing feature of the ninth embodiment.

According to FIG. 13a, the strips 21, 21' are mounted on the body 3 at the time of insertion of the cage. The ancillary placement element comprises notably a piece 22, for example of rectangular shape, suitable for being fitted into, or otherwise secured to, the posterior part of the body 3. This piece 22 clamps the strips 21, 21' and helps to keep them in the grooves 16, 16'. It also helps to transmit the rotational force applied to the handle 221 of the ancillary. The cage body 3 comprises, on its posterior side, a screw pitch 223 in order to be able to screw an instrument 222 into it. This instrument 222 slides inside the piece 22 and makes it possible to push the body 3 after the rotation of the latter has been achieved. In a variant embodiment (not shown), the body 3 is not pushed individually, but it is the strips 21, 21' that are withdrawn once the body 3 is in its desired position. Naturally, any other placement system associating strips 21, 21' with a body 3 can be used for the purposes of expansion and insertion of the body 3.

Figures 12A, 12B:
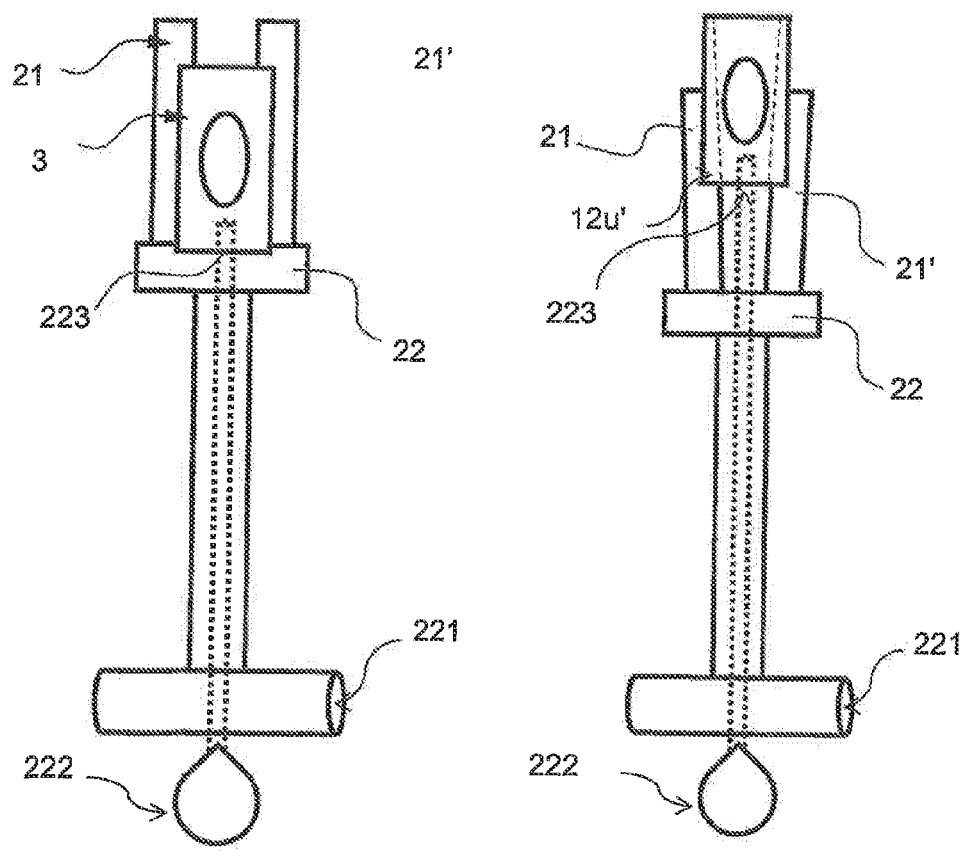
FIG. 12a represents a top view of the cage and of the ancillary placement element in a first position.
FIG. 12b represents a top view of a similar cage and of a similar ancillary placement element in a second position.

The strips 21, 21' can also be positioned in an intermediate position (FIG. 12b), or even on the periphery of the posterior face of the body 3, notably if it is desired to reduce the width of the cage at the moment of its passage into the rachidian canal. The depth of the grooves 16, 16' is not necessarily constant and may decrease from the rear to the front of the body 3 (FIG. 12b). Similarly, it is possible for the strips 21, 21' not to be aligned in two parallel axes (FIG. 12b), and/or to have a nonconstant, or increasing or decreasing width.

Figure 12C:
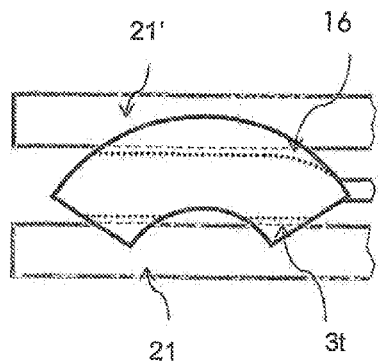
FIGS. 12c and 12d represent a top view of a cage of arched shape according to a variant embodiment in two successive positions.
Figure 12D:
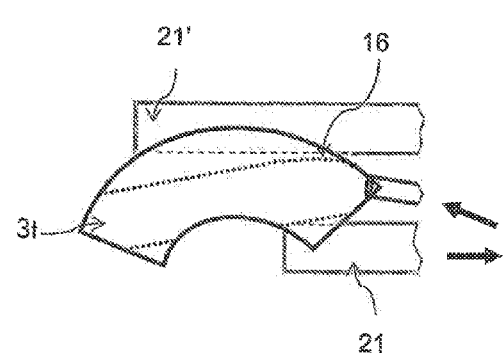

FIGS. 12c and 12d represent a variant of a cage comprising an arched body so as to better conform to the shape of the contour of the vertebral bodies, whether it be for a posterior or transforaminal or lateral approach. Once the cage body 3 is close to its final position, the strip 21 that is on the concave side of the body 3 is withdrawn and pressure is applied to said body 3 via the instrument 222 in an axis that is oblique relative to the longitudinal axis so as to be able to make it pivot on an axial or sagittal plane (on the assumption that the strips are in a position of distraction of the intersomatic space).

Figure 13:
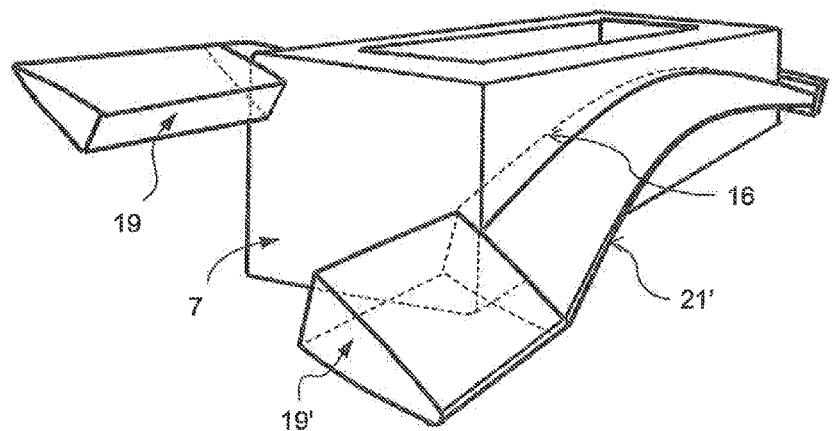
FIG. 13 represents a view in perspective of a cage according to a 13th embodiment.

FIG. 13 represents a 13th embodiment combining the features of the insertion flaps of the ninth embodiment with the retractable strips of the 12th embodiment, namely in which the cage body 3 comprises on each of these lateral sides an arched longitudinal groove 16, 16' into which the arched strips 21, 21' that form an integral part of an ancillary placement element are inserted. There are multiple variant embodiments, because the strips can also be straight or in a plane that differs from the plane of the flaps and the strips can also be combined with an insertion tongue of the fifth embodiment.

Figure 14:
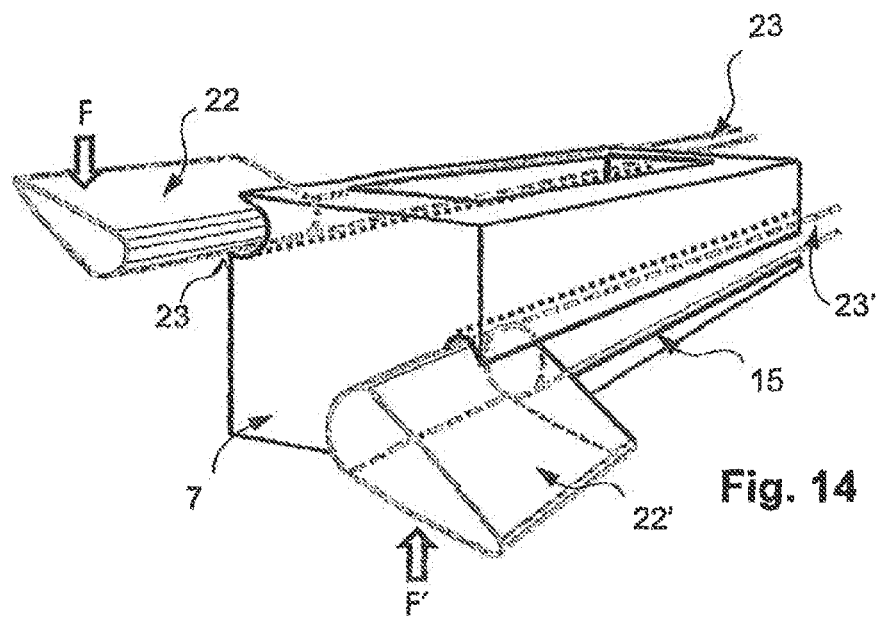
FIG. 14 represents a view in perspective of a cage with flaps according to a 14th embodiment.

According to a 14th embodiment (FIG. 14), a first and a second removable flap 22, 22' is attached on the end respectively of a first and second rods 23, 23' arranged in a first and second grooves 16, 16', said grooves being situated along one and the other of the lateral sides, respectively in the superior part and inferior part of the body 3. The flaps 22, 22' may already be in place when the cage is inserted or may be slid into the grooves 16, 16' after the body 3 has been inserted in order to achieve the rotation. The value of this cage is that it is possible to retract these flaps 22, 22' after exercising rotation of the cage. The profile of the cross section of each groove 15, 15' prevents the flaps 22, 22' from rotating about their rod 23, 23' when the vertebrae exert a force "F" and "F1" against said flaps.

Figure 14A:
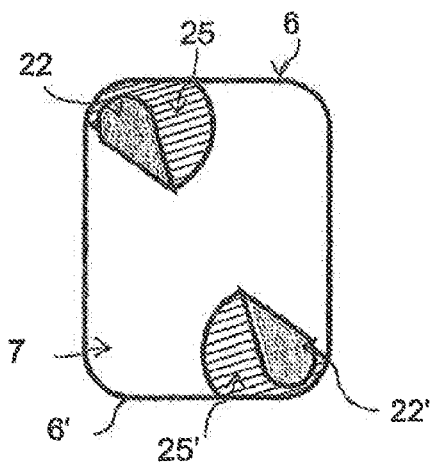
FIGS. 14a and 14b represent a front view of the cage with removable flaps in a retracted and deployed position.
Figure 14B:
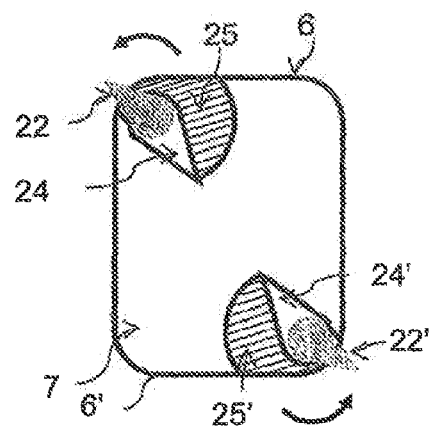
Figure 14C:
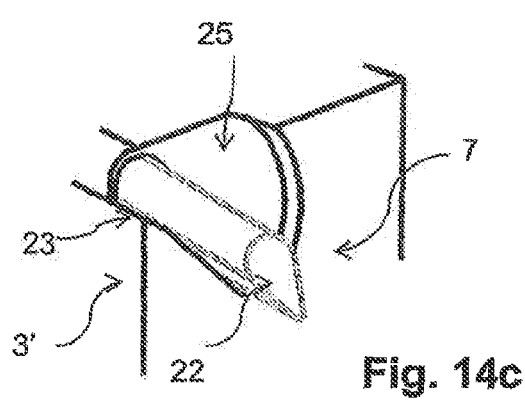

A variant embodiment illustrated by FIGS. 14a, 14b and 14c consist in inserting the flaps 22, 22' into ducts 24, 24' passing through the body lengthwise and comprising a cross section corresponding to that of the flaps. Two rotational enclosures 25, 25' arranged on the anterior side 7 of the body allow the flaps 22, 22' to accomplish an arc of a circle up to the abutment 23 (FIG. 14c) in order to be able to be deployed in their protruding position in situ in order therein to fulfill their lever-arm function. The cage is inserted with or without flaps through the rachidian canal. In contact with the anterior side 7 of the body with the vertebrae, the flaps 22, 22' are pushed via their respective rod 23, 23' into the ducts 24, 24' until they emerge in their respective rotational enclosures 25, 25'. If the flaps are already in their ducts when the cage is inserted, they simply have to be deployed. The deployment takes place via a rotation of the order of 190° of the rods which rotates the flaps 22, 22' up to the abutment 23. The flaps are then inserted into the intersomatic space and the body is rotated for the purposes of expansion. The abutment resists the force "F" exerted by the vertebra. In order to further stabilize the lever arm, the rods may be directly attached to the body 3, for example in its posterior part, or conversely only to the insertion device of the body. As a variant, the flaps can be deployed immediately when the body is inserted through the rachidian canal, then, after the rotation of the body, the flaps are folded back into their entrance position as shown in FIGS. 14a and 14b, then retracted from the body along their duct. If the surface of the vertebra prevents such a reverse rotation of the flaps, the flaps can be pushed forward past the end of the abutment 23 and then complete the rotation and be retracted from the body. Such a device can also combine a movable flap and a fixed flap, or a movable flap and a rod. A variant embodiment consists in furnishing the body with deployable then semi-retractable flaps, that is to say that they are not retracted with the placement device after the body is inserted, but are retracted inside the body in order to limit the space requirement of the intersomatic space.

It goes without saying that certain features of any embodiment can be substituted and/or added to certain features of one of the other embodiments. In particular, each of the features joined to the body of the cage, insertion tongue, flaps, insertion rods, wings, can be made in a resorbable material designed to disappear in order to leave room for the bony growth, or an osteoconductive material designed to promote said bony growth.

All the variants are also capable of being applied to cages which are not designed to be inserted via a posterior approach, notably to cages for transforaminal or lateral approaches.

Moreover, the end of the part designed to expand the intervertebral space has, in certain embodiments, a bevelled profile. Moreover, all the sharp edges of the body can be blunted. Convex or concave surfaces can also be produced on the side of the body 3 containing the part designed to expand the intersomatic space in order to make the transition between this part and said body 3 easier.

Finally, the subject of the present invention also relates to two methods for inserting the cage into the intersomatic space. More particularly, the invention relates to a first method for inserting the cage as described in certain of the preceding embodiments, said method comprising the following steps:

the cage is inserted into the rachidian canal with its insertion tongue 2 vertical until the front of the insertion tongue 2 is in contact with the vertebrae;

the cage is then turned a quarter turn or an angle substantially less than 90° in order to tilt the insertion tongue 2 to the horizontal which allows it to be inserted into the slightly expanded intervertebral space;

the cage is then again turned a quarter turn or an angle substantially less than 90°, but in the opposite direction to the second step, which has the effect of expanding the intervertebral space to a height close to the height H' of the insertion tongue 2 of the cage;

the latter is then pushed or, if necessary, impacted, into the intervertebral space to its final position.

The invention also relates to a second method for inserting a cage as described in other preceding embodiments, said method comprising the following steps:

the cage is inserted into the rachidian canal until the front of said cage is in contact with the vertebrae;

a pressure and/or impaction is applied to the cage causing an autorotation movement of the latter allowing the expansion of the intersomatic space;

an additional pressure is then applied to the cage in order to insert it into the intersomatic space up to its final position.

The invention claimed is:

1. A method for inserting an intersomatic cage in an intersomatic space between two vertebrae, the intersomatic cage comprising a body of rectangular or trapezoidal cross-section that has an essentially flat superior surface capable of resting against a superior vertebra and an essentially flat inferior surface capable of resting against an inferior vertebra and at least one part that extends from said body and is configured for dilating the intersomatic space in response to rotation of the intersomatic cage after insertion of said at least one part in the intersomatic space between the superior vertebra and the inferior vertebra, wherein the method comprises the successive steps of:
a) inserting said at least one part, but not said body from which said at least one part extends, in the intersomatic space between said superior and inferior vertebrae,
b) then rotating the intersomatic cage in a given direction of rotation by an angle up to 90°, such that the intersomatic space is dilated by said at least one part to a spacing which is superior to the distance between the essentially flat superior surface and the essentially flat inferior surface of the body of the intersomatic cage,
c) inserting the body of the intersomatic cage into the thus-dilated intersomatic space by pushing the body of the intersomatic cage into the thus-dilated intersomatic space, and
d) counter-rotating the intersomatic cage in a direction opposite to the direction of rotation in step b), or allowing the intersomatic cage to counter-rotate in a direction opposite to the direction of rotation in step b), until the essentially flat superior and inferior surfaces of the body of the intersomatic cage come to rest against the superior and inferior vertebra.

2. The method according to claim 1, wherein in step b), the intersomatic cage is rotated by an angle less than 90° in said given direction of rotation.

3. The method according to claim 2, wherein said at least one part is retractable into the body of the intersomatic cage or is fully removable from the body of the intersomatic cage and is retracted or removed after step d) of claim 1.

4. The method according to claim 1, wherein in step d) the intersomatic cage is allowed to counter-rotate in the direction opposite to the direction of rotation in step b) through compression of the intersomatic cage between the superior and inferior vertebrae, without applying an external rotational force to the intersomatic cage, until the essentially flat superior and inferior surfaces of the body of the intersomatic cage come to rest against the superior and inferior vertebrae.

5. The method according to claim 1, wherein said at least one part is retractable into the body of the intersomatic cage or is fully removable from the body of the intersomatic cage and is retracted or removed after step d) of claim 1.

6. The method according to claim 1, wherein one said part, or a plane defined by two said parts, is arranged in an inclined plane relative to the essentially flat superior and inferior surfaces of the body of the intersomatic cage.

7. The method according to claim 6, wherein the angle of said inclined plane is comprised between 40° and 60° relative to the essentially flat superior and inferior surfaces of the body of the intersomatic cage.

8. The method according to claim 1, wherein the intersomatic cage is rotated in step b) by an angle between 40° and 60°.

9. The method according to claim 1, wherein said at least one part of the intersomatic cage comprises a part having a distal end and a proximal end which is connected to a face of the body of the intersomatic cage, said part extending over a width from the proximal part connected to the body to the distal part, said part having a cross-section in a sectional plane facing to said face of the body which cross-section has a short dimension and a long dimension, the intersomatic cage comprising an inclined first plane defined by and extending along the entire long dimension of said part and extending through the middle of the short dimension along the entire length of the long dimension and extending across the width of said part, which inclined first plane is arranged at an angle that is inclined up to 90° relative to the essentially flat superior and inferior surfaces of the body of the intersomatic cage, said inclined first plane intersecting with a second plane in extension of said essentially flat superior surface of the body at a first end of the long dimension of the part, said inclined first plane furthermore intersecting with a third plane in extension of said essentially flat inferior surface of the body at a second end of the long dimension of said part.

10. The method according to claim 9, wherein said inclined plane of the intersomatic cage is arranged at an angle that is inclined between 40° and 60° relative to the essentially flat superior and inferior surfaces of the body of the intersomatic cage.

11. The method according to claim 1, wherein the body of rectangular or trapezoidal cross-section of the intersomatic cage has blunted edges.

12. The method according to claim 1, wherein the intersomatic cage is rotated in step b) by an ancillary placement element.

* * * * *